United States Patent [19]

Thakkar

[11] 4,024,240

[45] May 17, 1977

[54] ANTIBIOTIC A-32390 COMPOSITIONS

[75] Inventor: Arvind L. Thakkar, Indianapolis, Ind.

[73] Assignee: Eli Lilly and Company, Indianapolis, Ind.

[22] Filed: July 18, 1975

[21] Appl. No.: 597,115

[52] U.S. Cl. .................................. 424/80; 424/304
[51] Int. Cl.² ................ A61K 31/79; A61K 31/275
[58] Field of Search ............................. 424/80, 304

[56] References Cited

UNITED STATES PATENTS

| | | | |
|---|---|---|---|
| 3,419,596 | 12/1968 | Fetzev | 260/464 X |
| 3,636,036 | 1/1972 | Ug | 260/464 X |
| 3,712,911 | 1/1973 | Schoellkops et al. | 260/465.4 X |

*Primary Examiner*—Jerome D. Goldberg
*Attorney, Agent, or Firm*—Nancy J. Harrison; Everet F. Smith

[57] ABSTRACT

Novel A-32390:PVP compositions useful in the treatment of fungal infections.

4 Claims, No Drawings

ANTIBIOTIC A-32390 COMPOSITIONS

BACKGROUND OF THE INVENTION

Antibiotic A-32390 factor A and the tetra-($C_2$–$C_4$)-acyl ester derivatives of A-32390 factor A are described in a copending U.S. application of Gary G. Marconi and Marvin W. Hoehn, titled ANTIBIOTIC A-32390 AND PROCESS FOR PREPARATION THEREOF, Ser. No. 597,112, filed this even date herewith.

Polyvinylpyrrolidone (PVP) is a polymer which has unusual complexing and colloidal properties and is generally physiologically inert. PVP has a wide variety of uses. It has been used in pharmaceuticals, cosmetics and toiletries, textiles, detergents, beverages, pigments, automotive products, plastics, and as a plasma extender. PVP has been used in pharmaceuticals as a suspending agent, as a tablet binder and/or coating agent in layered tablets and in timed-release capsules, to stabilize vitamins and aspirin tablets, and to reduce drug irritation in ophthalmic and topical preparations. The stable complex which PVP forms with iodine has been used as a germicidal preparation. PVP has also been used to increase the solubility of aromatic compounds including several useful drugs. For example, U.S. Pat. No. 3,673,163, described a co-precipitate of acronycine with PVP which provided an acronycine dosage form having increased solubility. PVP has also been used with 1-hydroxy-3-(1′,1′-dimethylheptyl)-6,6-dimethyl-6,6a,7,8, 10,10a-hexahydro-9H-dibenzo[b,d]pyran-9-one) in order to enhance and retain the absorption characteristics of this drug over a prolonged period of time. When PVP has been used in combination with an antibiotic, the PVP has either been used as a binding agent (See U.S. Pat. No. 3,577,514), to sustain the release of the antibiotic (See U.S. Pat. No. 3,485,914 and U.S. Pat. No. 3,499,959) or to make the antibiotic more soluble (See U.S. Pat. No. 3,674,859). No compositions containing PVP and an antibiotic with a chemical structure resembling that of A-32390 factor A are known.

SUMMARY OF THE INVENTION

This invention provides solid dispersions of a compound selected from the group consisting of antibiotic A-32390 factor A and the tetra-($C_2$–$C_4$)-acyl esters thereof with a PVP having a molecular weight in the range of from 10,000 to 360,000.

DETAILED DESCRIPTION OF THE INVENTION

This invention relates to novel, therapeutically-useful solid dispersions. These dispersions consist of a compound selected from the group consisting of antibiotic A-32390 factor A and the tetra-($C_2$–$C_4$)-acyl ester derivatives thereof with a polyvinylpyrrolidone (PVP) having a molecular weight in the range of from about 10,000 to about 360,000. Antibiotic A-32390 factor A is a white crystalline compound which is soluble in dimethylformamide, dimethylacetamide and dimethyl sulfoxide; slightly soluble in acetone, ethyl acetate, chloroform and lower alcohols; but is substantially insoluble in water, benzene, hexane, diethyl ether and carbon tetrachloride; and which has:

a. a melting point of about 162° C;
b. a molecular weight of 396, as determined by mass spectrometry;
c. a specific rotation of +17° (c=1, dimethylformamide);
d. an approximate elemental composition of 54.63 percent carbon, 6.03 percent hydrogen, 7.38 percent nitrogen, and 31.96 percent oxygen;
e. an empirical formula of $C_{18}H_{24}N_2O_8$;
f. an infrared absorption spectrum in mineral oil mull with the following distinguishable absorption maxima (w=weak; m=medium; s=strong): 2.92(s), 4.64(m), 5.73(m-s), 5.76(m-s), 6.14(w-m), 7.54(m), 7.74(m), 7.89(w), 8.08(m-s), 8.21(w-m), 8.80(w), 9.15(m-s), 9.40(w), 9.60(w), 10.25(w), 10.45(w-m), 11.05(w), 11.20(w), 12.22(w), 13.00(w-m) and 13.16(w) microns;
g. a nuclear magnetic resonance spectrum in dimethyl sulfoxide with the following characteristics: $\delta$2.11 (s), 2.24 (s), 3.61 (dd, J= 9, 7 Hz), 3.77 (dddd, J= 9, 6, 5.5, 2 Hz), 4.21 (dd, J= 11, 6 Hz), 4.45 (dd, J= 11, 2 Hz), 4.42 (exchangeable d, J= 7 Hz) and 4.91 ppm (exchangeable d, J= 5.5 Hz);
h. an observed absorption maximum, $\lambda_{max}$, in 95 percent ethanol in its ultraviolet spectrum at 230 mm ($\epsilon$ 27,900);
i. a characteristic X-ray powder diffraction pattern (chromium radiation, 2.2896Å, vanadium filter), having the following interplanar spacings in angstroms (d):

| d | Relative Intensity |
|---|---|
| 18.75 | 100 |
| 9.33 | 50 |
| 7.48 | 10 |
| 6.93 | 10 |
| 6.46 | 70 |
| 6.11 | 40 |
| 5.17 | 70 |
| 4.77 | 30 |
| 4.54 | 30 |
| 4.27 | 30 |
| 3.76 | 10 |
| 3.60 | 70 |
| 3.46 | 60 |
| 3.33 | 05 |
| 3.25 | 30 |
| 3.02 | 05 |
| 2.48 | 05 |
| 2.37 | 05 | j. an $R_f$ value of 0.32 on thin-layer chromatography over silica gel in a chloroform-methanol (9:1) solvent system, using Sarcina lutea ATCC 9341 as the detection organism Antibiotic A-32390 factor A has been determined to have the following structure:

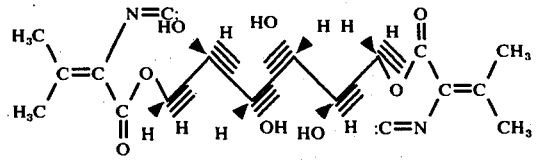

which structure is designated 1,6-di-O-(2-isocyanao-3-methylcrotonyl)-D-mannitol.

Antibiotic A-32390 has four hydroxyl groups. The tetra-($C_2$–$C_4$)-acyl ester derivatives of A-32390 factor A are prepared by esterification of these hydroxyl groups using standard procedures. Antibiotic A-32390 factor A and the tetra-($C_2$–$C_4$)-acyl ester derivatives of A-32390 factor A can be represented by the structural formula

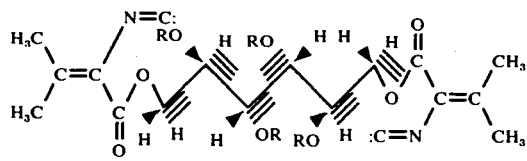

wherein all R's are the same and are selected from the group consisting of hydrogen, acetyl, propionyl and butyryl. For the sake of brevity, a compound having the above-described formula will be arbitrarily designated herein as an A-32390 compound. The A-32390 compounds are antifungal, antibacterial, and hypotensive agents.

Antibiotic A-32390 factor A is prepared by submerged aerobic fermentation of Pyrenochaeta sp. NRRL 5786 and is recovered in the A-32390 antibiotic complex by extraction of the broth. Individual factor A is separated from the A-32390 complex by chromatography.

A culture of the A-32390-producing organism has been deposited with the permanent culture collection of the U.S. Department of Agriculture, Agricultural Research Service, Northern Regional Research Laboratory, Peoria, Ill. 61604, where it has been deposited without restriction as to availability and has been accorded the accession No. NRRL5786.

As is customary in aerobic, submerged culture processes, sterile air is blown through the culture medium during the fermentation process. For efficient organism growth and antibiotic production, the volume of air employed is preferably in excess of about 0.1 volume of air per volume of culture medium per minute (V/V/M). In submerged aerobic fermentation of the A-32390 antibiotics, optimal yields are obtained when the volume of air employed is at least 0.3 V/V/M.

In general, when submerged aerobic fermentation conditions or shake-flask culture conditions are employed, maximum production of the A-32390 antibiotics occurs between about 3 to about 6 days after the inoculation of the culture medium. Maximum production of A-32390 antibiotics in large-scale fermentation tanks under submerged aerobic conditions occurs at about 96 hours.

The course of the fermentation can be followed by assaying the fermentation medium from time to time against an organism susceptible to the A-32390 antibiotics. One such organism which can be employed is *Sarcina lutea* ATCC 9341.

Following production under submerged aerobic fermentation conditions, the A-32390 antibiotics can be recovered as a complex from the fermentation broth by methods commonly employed in the fermentation art. The filtered broth contains the major portion of the A-32390 antibiotics produced during fermentation. The mycelium contains a relatively small amount of the A-32390 antibiotics produced.

Under the conditions employed thus far, the organism designated as Pyrenochaeta sp. NRRL 5786 produces factor A as the predominant factor. In general, factor A is present in amounts from about 60 to about 95 percent of the total recovered A-32390 antibiotics.

The A-32390 antibiotics are recovered from the fermentation medium as an antibiotic complex. Since the majority of antibiotic activity is associated with the broth, a preferred method of recovery is filtration of the fermentation medium.

The filtered fermentation broth is then extracted with a suitable organic solvent. The resulting extract is treated with a drying agent and then is concentrated to a small volume to give the A-32390 antibiotic complex as a crude semicrystalline solid precipitate.

Solvents which are esters, such as ethyl acetate, amyl acetate and isoamyl acetate, are suitable solvents with which to extract the filtered broth. Ethyl acetate is a preferred solvent for extraction.

An alternate method of recovering the A-32390 antibiotic complex is by adsorption onto a macroreticular resin such as Amberlite XAD-2 or XAD-4 (Rohm and Haas). Acetone is a particularly useful eluting solvent for this procedure.

Alternatively, the whole fermentation broth can be extracted with a suitable water-immiscible solvent, such as ethyl acetate; and this extract can be concentrated as above to obtain the A-32390 antibiotic complex.

The A-32390 antibiotic complex can be further purified by methods such as fractional crystallization or chromatography over a suitable absorbent. Suitable adsorbents include silica gel, magnesium silicate, and the like.

Antibiotic A-32390 factor A is separated and isolated as an individual compound most readily by a combination of fractional crystallization and chromatographic methods. For example, factor A is isolated from the A-32390 antibiotic complex by chromatography over silica gel and subsequent crystallization from acetone. Minor factors B, C, and D are present in the mother liquor after crystallization and separation of factor A.

The use of A-32390 compounds as antifungal agents is set forth more explicitly in the above-described co-pending application of Marconi et al. According to this specification, the dosage of A-32390 compound will vary from about 120 to about 600 mg/kg of animal-body weight per day. With the dispersions of the present invention, dosages as low as about 30 mg/kg of animal-body weight per day are useful in the treatment of fungal infections.

The dispersions of the present invention contain one part of an A-32390 compound together with from one to fifteen parts of a PVP having a molecular weight in the range of from about 10,000 to about 360,000. PVP can be prepared by well-known methods. Four grades of PVP are commercially available: K-15, K-30, K-60, and K-90 which have average molecular weights of about 10,000, 40,000, 160,000 and 360,000, respectively. Although the molecular weight of the PVP is not a critical feature of the dispersions of this invention, especially-preferred dispersions are those prepared with a PVP having a molecular weight in the range of from about 10,000 to about 60,000, for example, the commercially-available PVP having a molecular weight of about 40,000.

The state in which the A-32390 compounds exist in the A-32390:PVP dispersions of this invention is not known. It is believed that possibly the A-32390 compounds exist in these dispersions in an extremely finely-divided crystalline state, in an amorphous state, or as a complex with the PVP.

The dispersions are prepared by dissolving the A-32390 compound and the PVP separately in like or unlike solvents, mixing the two solutions and evaporating the resulting solution. Suitable solvents for dissolving the A-32390 compounds include dimethylformamide, chloroform, dimethylacetamide, dimethyl sulfoxide and acetone. PVP is soluble in a wide variety of solvents. Dimethylformamide, chloroform and dimethyl sulfoxide are especially preferable solvents for the preparation of A-32390:PVP dispersions because both the A-32390 compounds and PVP are soluble in these solvents.

The A-32390:PVP dispersions of this invention are especially useful for the administration of the A-32390 factor A tetra-($C_2$-$C_4$)-acyl esters. These acyl esters are liquids which are difficult and cumbersome to manipulate. The corresponding A-32390:PVP dispersions prepared from the acyl esters are solids which are easier to handle.

The A-32390:PVP dispersions of this invention provide a more bioavailable form of A-32390 compound. The increased bioavailability of the A-32390 compounds in these dispersions is apparently not due to an increase in solubility. For example, the A-32390 dispersions show approximately the same in vitro activity against *Candida albicans* as that exhibited by the non-dispersed A-32390 factor A and its esters.

As the amount of PVP increases in the dispersions of this invention, the amount of A-32390 compound required for effectiveness decreases. This is demonstrated by an in vivo test against *Candida albicans* in mice. In this test, *Candida albicans*-infected mice were treated 3 times with subcutaneous doses of A-32390:PVP dispersions in which the A-32390 compound was factor A (R's=H) and the PVP was of molecular weight 40,000. Table I summarizes the lowest levels at which several of these A-32390:PVP dispersions exhibited activity against *Candida albicans*.

TABLE I

| A-32390:PVP Ratio | Lowest Level Exhibiting Activity (mg/kg × 3) |
|---|---|
| 1:0 (No PVP) | 50.0 |
| 1:1 | 25.0 |
| 1:2 | 66.0 |
| 1:3 | 12.5 |
| 1:4 | 15.0 |
| 1:9 | 7.5 |
| 1:24 | No activity |
| 0:1 (PVP only) | No activity |

It is frequently advantageous to add a small amount of wetting agent such as, for example, polyoxyethylene (20) sorbitan mono-oleate, to the dispersions of this invention. Such a wetting agent serves to properly wet and suspend the relatively hydrophobic and insoluble A-32390 compound in water for administration. A convenient method of preparing such dispersions is to dissolve the wetting agent, the PVP, and the A-32390 antibiotic compound separately in appropriate solvents; the three solutions are then mixed and evaporated together to give the desired dispersion.

The dispersions of this invention are administered parenterally and are conveniently formulated by suspending an appropriate amount of dispersion in any suitable aqueous vehicle prior to administration.

The following examples are provided in order to more fully illustrate the dispersions of the present invention.

EXAMPLE 1

PREPARATION OF A-32390 FACTOR A

A. Production of A-32390

A culture of *Pyrenochaeta* sp. 5786 was prepared on an agar slant having the following composition:

| Ingredient | Amount |
|---|---|
| Agar (Meer, washed three times) | 20.00 g |
| Dextrose | 20.00 g |
| Peptone | 5.00 g |
| $KH_2PO_4$ | .50 g |
| $MgSO_4 \cdot 7H_2O$ | .02 g |
| $FeSO_4 \cdot 7H_2O$ | .01 g |
| Deionized water | q.s. 1 liter |

The pH of this medium was adjusted to pH 6.2 by the addition of sodium hydroxide. The pH of the medium after sterilization is approximately 5.4.

The slant was inoculated with *Pyrenochaeta* sp. NRRL 5786, and the inoculated slant was incubated at 25° C for 7 days.

One-half of the mature slant culture was scraped with a sterile needle and used to inoculate 50 ml of a vegetative medium having the following composition:

| Ingredient | Amount |
|---|---|
| Glucose | 25 g |
| Edible molasses | 36 g |
| Corn-steep liquor | 6 g |
| Malt extract | 10 g |
| N-Z Case* | 10 g |
| Czapek's Mineral Stock** | 2 ml |
| Deionized water | q.s. 1100 ml |

*Enzymatic digest of casein, Sheffield Chemical Co., Norwich, New York
**Czapek's Mineral Stock has the following composition:

| Ingredient | Amount |
|---|---|
| $FeSO_4 \cdot 7H_2O$ (Dissolved in 2 ml conc. HCl) | 2 g |
| KCl | 100 g |
| $MgSO_4 \cdot 7H_2O$ | 100 g |
| Deionized water | q.s. to 1 liter |

The inoculated vegetative medium was incubated in a 250-ml Erlenmeyer flask for 2 days at 25° C on a shaker rotating through an arc 2 inches in diameter at 250 rpm.

This incubated vegetative medium may be used directly to incubate the second-stage vegetative medium, or, alternatively, it can be preserved in storage by maintaining the culture in the vapor phase of liquid nitrogen. The culture is prepared for later use in multiple small vials as follows: In each vial is placed 2 ml of incubated vegetative medium and 2 ml of a glycerol-lactose solution having the following composition:

| Ingredient | Amount |
|---|---|
| Glycerol | 200 g |
| Lactose | 100 g |
| Deionized water | q.s. 1 liter |

The prepared suspensions are stored in the vapor phase of liquid nitrogen.

The stored suspension (1 ml) was used to inoculate 50 ml of a first-stage vegetative medium having the same composition earlier-described for the vegetative medium. Two replicate inoculated flasks (250 ml) were incubated for 2 days at 25° C on shakers rotating through arcs of 2 inches at 250 rpm.

In order to provide a larger volume of inoculum, 10 ml of the incubated first-stage vegetative medium was used to inoculate 200 ml of a second-stage vegetative medium also having the same composition as that of the vegetative medium. Four replicate included flasks (1-liter volume) were incubated for one day at 25° C on shakers rotating through arcs of 2 inches at 250 rpm.

The incubated second-stage vegetative medium (800 ml) was used to inoculate 100 liters of sterile production medium having the following composition:

| Ingredient | Amount |
| --- | --- |
| Sucrose | 30.00 g/l. |
| Glucose | 15.00 g/l. |
| Cottonseed flour | 5.00 g/l. |
| KCl | 0.50 g/l. |
| $K_2HPO_4$ | 0.20 g/l. |
| $FeSO_4 . 7H_2O$ | 0.01 g/l. |
| $NaNO_3$ | 0.50 g/l. |
| $MgSO_4 . 7H_2O$ | 0.50 g/l. |
| Antifoam Agents | 0.70 g/l. |
| Czapek's Mineral Stock | 2.00 ml/l. |
| Ethanol (95%) | 14.00 ml/l. |
| Deionized water | q.s. 1 liter |

This medium had an unadjusted pH of 6.6. Adjustment to pH 7.3 was made by the addition of approximately 10 ml of 10 N sodium hydroxide before sterilization. The medium had a pH of 6.4 after sterilization at 120° C for 30 minutes at 16 to 18 pounds pressure.

The inoculated production medium was allowed to ferment in a 165-liter fermentation tank for four days at a temperature of 25° C. During this time, the fermentation medium was aerated with sterile air at the rate of 0.25. V/V/M. The medium was stirred with conventional agitators at 200 rpm.

B. Separation of the A-32390 Antibiotic Complex

This fermentation broth (100 liters) was filtered, using 3–5 percent of a filter aid (Hyflo Supercel). The broth filtrate (about pH 7.0) thus obtained was extracted with ethyl acetate (two 60-liter portions). The combined ethyl acetate extracts were evaporated under vacuum to a volume of one liter. This solution was cooled (5° C) for 24 hours. The semicrystalline precipitate which formed was separated by filtration, washed with cold ethyl acetate (50 ml), and dried under vacuum to give the A-32390 antibiotic complex.

C. Isolation of A-32390 Factor A

A-32390 antibiotic complex (5 g), prepared as described in B above, was slurried in benzene (100 ml). This slurry was applied to a 3.7—X 90-cm silica gel (Matheson, grade 62) column prepared in benzene. The column was eluted successively with benzene (2 liters), 1:1 benzene-ethyl acetate (3 liters) and ethyl acetate (500 ml). Further elution with ethyl acetate (12.5 liters) separated the fractions containing A-32390 factor A. These fractions were combined and evaporated to dryness under vacuum. The residue thus obtained was dissolved in hot acetone (50 ml). A-32390 factor A crystallized upon cooling. Factor A was separated by filtration, washed with cold acetone (10 ml) and dried under vacuum (yield 1.5 g).

EXAMPLE 2

Preparation of A-32390 Factor A Tetraacetate

Antibiotic A-32390 factor A (206 mg), prepared as described in Example 1, was dissolved in dry distilled pyridine (5 ml). Acetic anhydride (2.5 ml) was added to this solution. The resulting solution was allowed to stand overnight at room temperature and then was concentrated under vacuum to a residue. This residue was redissolved in a water-acetone mixture, and the resulting solution was again evaporated under vacuum to a residue. The residue was repeatedly redissolved in chloroform and re-evaporated under vacuum until the resulting residue has no detectable pyridine odor.

The final residue, dissolved in 2 ml of chloroform, was placed on a silica-gel column (Grace, grade 62, 1.5 X 30 cm). The column was eluted with chloroform at a rate of about 3 ml/min. Twenty-five 15-ml fractions were collected. Active fractions (7–11) were combined and concentrated under vacuum to a syrupy residue. This residue was redissolved and re-evaporated from diethyl ether and then was dried under vacuum to give 268 mg of A-32390 factor A tetraacetate as a syrup (91% yield).

EXAMPLE 3

Antibiotic A-32390 factor A tetrapropionate derivative was prepared by following the procedure described in Example 2, by reaction of A-32390 factor A with propionic anhydride in pyridine.

EXAMPLE 4

Antibiotic A-32390 factor A tetrabutyrate derivative was prepared by the following the procedure described in Example 2, by reaction of A-32390 factor A with n-butyric anhydride in pyridine.

EXAMPLE 5

Preparation of A-32390:PVP Dispersions

A-32390:PVP dispersions were prepared by dissolving A-32390 factor A in acetone and dissolving PVP having a molecular weight of 40,000 in chloroform. The two solutions were mixed. Acetone and/or chloroform were added to the mixture until the solution was clear. The resulting solution was evaporated under vacuum to give a solid residue which was ground to a fine powder. A-32390:PVP dispersions prepared in this manner included the following:

| A-32390:PVP Ratio | Amount of A-32390 factor A | Amount of PVP |
| --- | --- | --- |
| 1:1 | 750 mg | 750 mg |
| 1:3 | 500 mg | 1500 mg |
| 1:4 | 500 mg | 2000 mg |
| 1:9 | 500 mg | 4500 mg |

EXAMPLE 6

Preparation of A-32390:PVP Dispersions Containing a Wetting Agent

A-32390:PVP dispersions containing a wetting agent were prepared by dissolving A-32390 factor A in acetone, dissolving PVP having a molecular weight of 40,000 in chloroform, and dissolving 0.01% Tween 80 (Polysorbate 80) in acetone (1 mg/ml). The three solutions were mixed. Acetone and/or chloroform were added to the mixture until the solution was clear. The resulting solution was evaporated under vacuum to give a solid residue which was ground to a fine powder. A-32390:PVP dispersions prepared in this manner included the following:

| A-32390:PVP Ratio | Amount of A-32390 factor A | Amount of PVP | Amount of Tween 80 |
| --- | --- | --- | --- |
| 1:1 | 750 mg | 750 mg | 150 mcg |
| 1:1 | 500 mg | 1500 mg | 200 mcg |
| 1:4 | 500 mg | 2000 mg | 250 mcg |
| 1:9 | 500 mg | 4500 mg | 500 mcg |

EXAMPLE 7

An A-32390:PVP dispersion having a ratio of 1:9 was prepared according to the method of Example 5 wherein the A-32390 compound was A-32390 factor A tetraacetate (R's are acetyl).

EXAMPLE 8

An A-32390:PVP dispersion having a ratio of 1:12 is prepared by dissolving 250 mg of A-32390 factor A tetrabutyrate (R's are n-butyryl) in dimethyl sulfoxide, dissolving 3,000 mg of PVP having a molecular weight of 160,000 in dimethyl sulfoxide, and mixing the two solutions. The resulting solution is evaporated under vacuum to give a solid residue which is ground to a fine powder.

I claim:

1. A solid antibiotic dispersion composition containing one part of an A-32390 compound of the formula

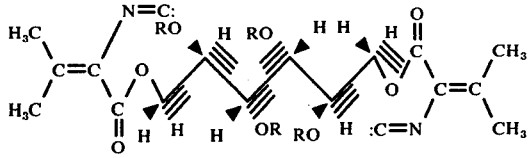

wherein all R's are the same and are selected from the group consisting of hydrogen, acetyl, propionyl and butyryl; and from 1–15 parts of a polyvinylpyrrolidone having a molecular weight in the range 10,000–360,000.

2. A dispersion according to claim 1 wherein the A-32390 compound is 1,6-di-O-(2-isocyano-3-methylcrotonyl)-D-mannitol.

3. A dispersion according to claim 1 containing one part of an A-32390 compound of the formula

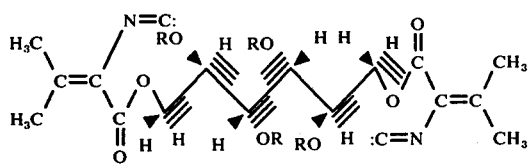

wherein all R's are the same and are selected from the group consisting of hydrogen, acetyl, propionyl and butyryl; and from 1–15 parts of a polyvinylpyrrolidone having a molecular weight in the range 10,000–60,000.

4. A dispersion according to claim 3 wherein the A-32390 compound is 1,6-di-O-(2-isocyano-3-methylcrotonyl)-D-mannitol.

* * * * *

UNITED STATES PATENT AND TRADEMARK OFFICE
CERTIFICATE OF CORRECTION

PATENT NO. : 4,024,240
DATED : May 17, 1977
INVENTOR(S) : Arvind L. Thakkar

It is certified that error appears in the above-identified patent and that said Letters Patent are hereby corrected as shown below:

Column 2, line 24, "mm ( 27,900);" should read
-- nm ($\epsilon$ 27,900); --.

Column 2, lines 55-60, the left-hand portion of the structural formula should appear as follows:

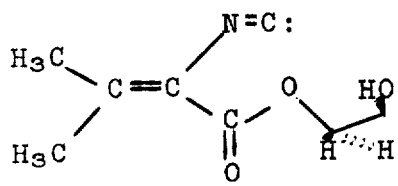

Columns 3, lines 5-10, and column 10, lines 1-8 and 20-28, the left-hand portion of the structural formula should appear as follows:

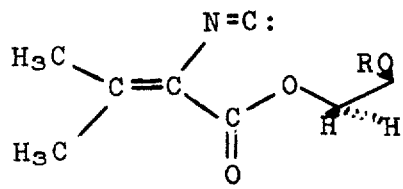

Signed and Sealed this

Twenty-fifth Day of April 1978

[SEAL]

Attest:

RUTH C. MASON
Attesting Officer

LUTRELLE F. PARKER
Acting Commissioner of Patents and Trademarks